United States Patent [19]

Barnes

[11] Patent Number: 5,112,461
[45] Date of Patent: May 12, 1992

[54] GELTRANS, A DEVICE FOR TRANSFER OF GEL TO PAPER

[76] Inventor: Wayne M. Barnes, 223 Renaldo Dr., Chesterfield, Mo. 63017

[21] Appl. No.: 521,758

[22] Filed: May 10, 1990

[51] Int. Cl.[5] .......................... C25B 1/00; B01D 61/42
[52] U.S. Cl. ............................... 204/182.8; 204/299 R
[58] Field of Search ........................ 204/299 R, 182.8

[56] References Cited

U.S. PATENT DOCUMENTS 4,849,078 7/1989 Love et al. .................. 204/299 R

*Primary Examiner*—John Niebling
*Assistant Examiner*—Caroline Koestner
*Attorney, Agent, or Firm*—Lyon & Lyon

[57] ABSTRACT

A support frame with multiple water jets, together with a support grid and carrier frame, is described. Methods for their construction from commonly available components, and methods for their use in a laboratory setting, are provided. This device semi-automates, and improves the quality and reliability of, an otherwise difficult and stressful step in DNA sequencing technology, namely the transfer of a thin and fragile gel from a glass plate to a sheet of filter paper for subsequent drying under vacuum.

8 Claims, 1 Drawing Sheet

GELTRANS, A DEVICE FOR TRANSFER OF GEL TO PAPER

INTRODUCTION

TECHNICAL FIELD

The device and method of its use find application in biological research and analysis and in forensic analysis, particularly for sequencing of DNA. The device is a novel instrument, similar to no other currently existing, which finds use at a step in DNA sequencing or other gel electrophoresis analysis, and step of transfer of the fragile gel to paper being, without the invention, a step of high stress to the technician and significant likelihood of damage to said gels.

BACKGROUND

DNA sequencing gel medium is a thin and fragile gel of 5 to 8% polyacrylamide, usually 0.4 mm in thickness (range 0.2 mm to 0.6 mm), and containing 7–8 M urea, and sometimes sucrose as solute, in addition to buffer electrolytes. If 35-S is used as the radionuclide label, the radioactvitity cannot penetrate either the thickness of the gel, dried urea in the gel, or even a thickness of plastic wrap. Therefore the gel must be washed free of urea and dried to a very thin layer lacking any water, and then exposed in direct contact with the X-Ray film. If 32-P is used as the radionuclide label, the gel may be autoradiographed while still wet and covering with plastic wrap, but increased resolution results from drying.

After the gel is run, the manipulations of soaking, fixing, and removal of the gel from one the glass gel plates, and placing it on a sheet of filter paper to dry down under vacuum, is a series of maneuvers requiring great skill and practice to avoid wrinkling, tearing or destroying the gel. Even for a practiced professional, this is a step of high psychological stress, since it comes near the end of the DNA sequencing procedure, and at the end of the most tedious, labor-intensive step of DNA sequencing. and the gel potentially contains data for many hundreds of nucleotides of DNA sequence.

RELEVANT LITERATURE

The most widely used collection of DNA analysis methods is Sambrook, Fritsch & Maniatis (1989). Their description of how to manually prepare a DNA sequencing gel by fixing and drying for autoradiograph is given in their section 13.56. A reading of this description makes clear how tricky it is, but it does not make clear that for many of the steps more than two hands would be of help. Each scientist must devise their own variation of this method that is consistent with their own level of coordination and experience.

The above referenced description may be paraphrased as follows: This description begins at the point of departure from my new method, just after the separation of one gel plate from the gel, leaving the gel stuck to one glass plate.

1) Soak gel, while it is still fixed on top of one of the the glass gel plates, in fixative (10% acetic acid, 10% methanol) and simultaneously remove urea, for a recommended time of 15 minutes.

2) Lift gel from fixative and drain by tilting slightly, holding the gel in place with one widely stretched, gloved hand.

3) Remove wrinkles and distortions.

4) Place dry filter paper on top of gel; in one quick, smooth motion, flip the sandwich upside down and lay down on the bench onto a sheet of protective paper.

5) Slide to the edge and off of the bench, allowing gel and paper to fall off of the plate [this is one step that, as described, could use a third hand; furthermore, stretching and wrinkle formation sometimes occur at this step].

6) Lay the gel onto another two sheets of filter paper. Apply the Saran wrap and dry under vacuum as usual.

The second-most popular collection of methods is Ausubel et al. (1989), whose section 7.4.8 describes the same procedure in a less complete and less accurate way.

There is nothing even similar to the invention, either in the literature or on the market.

SUMMARY OF THE INVENTION

A novel, frame-shaped device (the water-jet frame) supports a gel plate with gel stuck to its under side, suspended about 1 cm over the filter paper, which paper is supported by a grid. Tap water flow is turned on by the operator, and the water is conducted to little jets around 3 sides of the support frame. These jets point up at an angle to the edge of the gel. Only seconds are required to result in the gel being loosened from the plate to fall the short distance to the filter paper. The sides of the frame keep the gel from sliding sideways off the paper. The support grid allows the water and/or fixative level to be gently raised and lowered without dangerous (to the gel) manual handling of the gel.

Surprisingly, this water jet flow is essential to the loosening of the gel from the plate, since experimental soaking of the whole under water, without flow, does not result in the gel falling off of the glass plate onto the filter paper, even after 16 hours.

DESCRIPTION OF THE DRAWING

A drawing of the components of the device is presented in FIG. 1, as a complement to the detailed description given in the next section. The drawing is shown is exploded form, since the components actually rest in a stack together (in a shallow pan or tray with short sides and with a drain) during use.

DESCRIPTION OF THE SPECIFIC EMBODIMENTS

Figure 1:
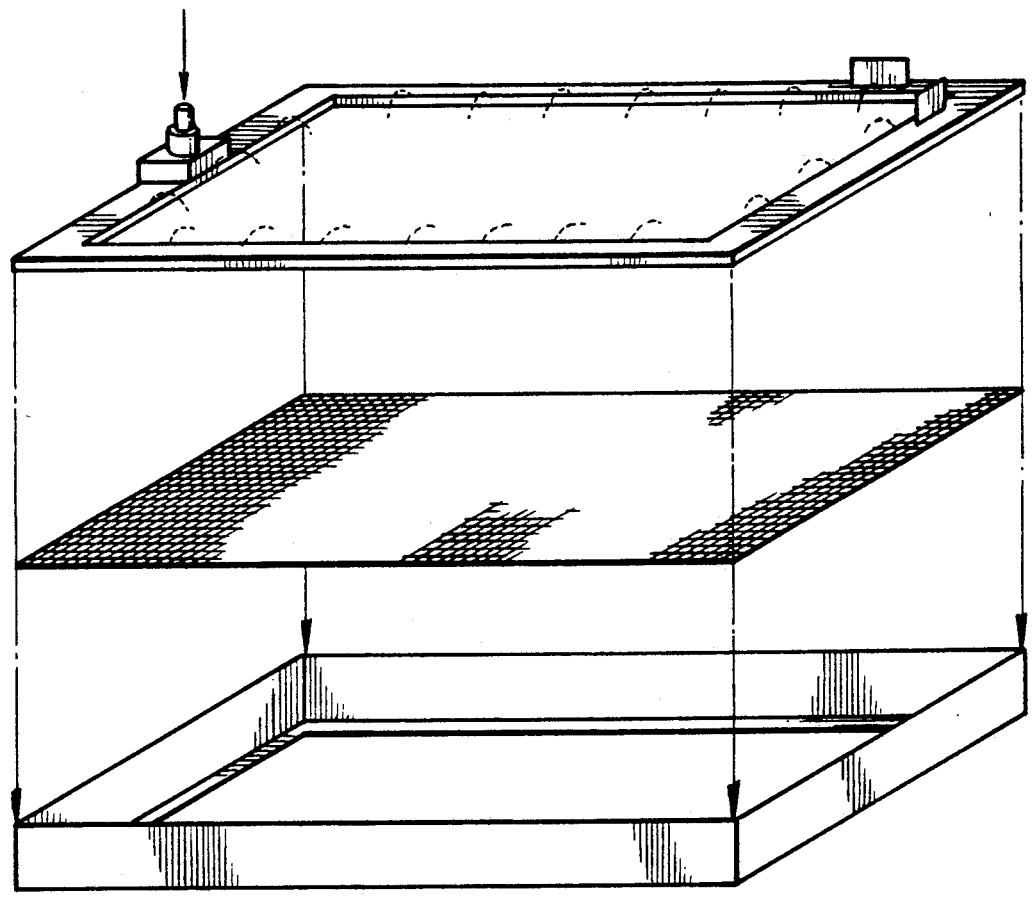

The following is intended to demonstrate examples of methods, materials and dimensions that may be used, and it is offered by way of illumination and not by way of limitation.

Constructs referred to below as "frame" are similar in shape to a picture frame, but they are laid flat on a horizontal bench during most steps of manufacture and description, such that the ¼" thickness of the Plexiglas is the vertical dimension.

Water-jet Frame.

The material is mostly clear acrylic (such as brands Plexiglas or Lucite), of ¼" thickness. All cut edges should be sanded or scraped smooth.

Two layers of ¼" Plexiglas constitute the water-jet frame, which is then ½" thick in its vertical dimension. The upper surface of the bottom layer, and the lower surface of the upper layer, are grooved so that the grooves form, when the layers are glued together, an inner water pipe (or "canal") that goes completely around the frame.

Cut Plexiglas into strips 3/4" wide. Cut to length two each of the following, based on the width W and length L of the larger of the two gel plates to be used for DNA sequencing gel electrophoresis. Relative rather than precise measurements are used throughout, since the frame must be sized to fit the actual sequencing gel plates in use, which come in many sizes.

| Piece no. | Length | For example, for W = 20 cm, L = 40 cm, use: |
|---|---|---|
| 1. | W − 0.5" | 7 3/8" |
| 2. | W + 1.0" | 8 7/8" |
| 3. | L + 0.25" | 16" |
| 4. | L + 1.75" | 17 1/2" |

For the odd-numbered pieces above, groove the center (center at 3/8") of one surface along the entire length, forming a groove of width 1/8" and depth 3/32" to 1/8. This is most conveniently done with a table saw set to provide only 3/32" above the table top. Two passes, one in each direction, will ensure that the groove is exactly centered from each side.

For the even-numbered pieces above, make the same grooves, but not to the ends—stop about 1" from each end. Continue the grooves with a table-top router, turning a 90° corner before the each end of the piece so that the groove comes out on the side, centered 3/8" from the end.

At one 1/4 from the end of one piece number 2, drill a 3/8" diameter hole in the center to intersect the groove. This will be the water entry point.

For the other piece number 2, and both of the pieces no. 3, drill the water-jet ports. These may also be drilled after gluing the frame together, but at that time drillings may clog the inner canal, and are somewhat problematic to remove. The jet port holes may be drilled with a 3/32" bit, at an approximate 40° angle from the horizontal, to connect the inside upper corner edge of the frame with the inner canal. It is tricky to drill right on the corner like this—first make a notch at the drill point with the side of the spinning bit.

Water Jet Positions

Position the water jet holes every two inches on the two sides of the frame, and on the end piece on the end away from the water entry. Do not drill water jet holes in the side of the frame containing the water entry port.

Glue the frame together with the grooves facing each other to form the inner water canal. Example gluing procedure: A suitable glue is methylene chloride thickened to a consistency of very light syrup with dissolved Plexiglas drillings. Apply the glue in a continuous bead to, for instance, one piece number 4 along the flat surface on either side of the groove. Then immediately place a piece number 3 onto that piece with its groove matching and the piece centered.

Water entry hose connector: In a bar of Plexiglas 1/2" thick and 1 1/4" wide, drill a 7/16" hole at 3/8" from one side and tap it with 1/4" plumbing thread; keep tapping until the tap protrudes 3/8" through the plastic. The cut 1/4" on either side of the hole and glue the piece over the entry port hole on the top of the frame, with the wide side of the tapped threads at the top. Allow this piece to protrude over the top of the frame on the inside. This will be a block to the bottom of the gel plate during use of the device. After the glue dries, screw in a hose connector (available in hardware stores made of either brass or plastic).

Six plate brackets, 1/4" × 3/4" × 2", should be glued on their long, 1/4" side, to the top of the frame near the corners on the sides with jet ports. The inside of these brackets should coincide with the inside of the inner water canal, so that the distance between the side brackets is just 1/8" wider than the width of the gel plates. After sanding to remove sharp edges, construction of the water-jet frame is complete. Label the top of the end away from the water entry with the words "TOP OF GEL".

Support Grid

Fluorescent light fixture light-scattering grid, white in color, made of plastic, about 1/2" thick and with 1/2" squares, is available in hardware stores. Cut a piece that is equal to the outside dimensions of the water jet frame or up to 7/16" less.

Surrounding Carrier Frame

A carrier frame may be constructed of Plexiglas. This frame is basically a fence 2 to 4" high made of 1/4" thick Plexiglas, with inner dimensions 1/4" larger than the outside dimensions of the frame, so that the support grid and frame fit inside it. Glue the fence to the top of a frame of 3/4" × 1/4" Plexiglas whose outer dimensions are exactly the same as the outer dimensions of the fence. This frame will then protrude 1/2" inside the fence, and serve as a support for the grid and the water-jet frame.

INSTRUCTIONS FOR USE OF THE INVENTION

My recommended procedure is summarized here. This procedure begins after the step of separating one glass gel plate from the gel, leaving the gel stuck to one of the plates, since this is the point of divergence from the standard prior art. This procedure is offered by way of illustration and not by way of limitation.

Recommended tray and drain, in which operations are carried out, is Bel-Art no. F16293 specifically modified to have drain spigot Bel-Art no. 30858. Any shallow, water-tight tray with a flat or slightly ridged bottom, and with a drain or siphon installed, may be used, providing its inner dimensions are large enough to accommodate the above carrier frame. The tray must be horizontal during use.

1) Lay two sheets of dry filter paper into the Gel-Trans frame, both sitting on the support grid and cut to size 1/4" narrower and 1/4" shorter than the inside dimensions of the frame, and briefly turn on the water jets until the paper is all wet; water jets of 3" to 4" of arc are the desired flow rate for this and the next step. If the filter paper expands and buckles slightly, pat it down on the buckles to flatten it. Approximate water flow time: 3 seconds.

2) Lay the gel plate with the gel still attached, upside down (gel on bottom) onto the frame. The frame is sized to support the glass plate along the edge, and the gel will be suspended within the frame, about 1 cm above the paper.

3) Turn on the tap water supply to the same flow rate as used for step 1. Usually within 15–20 seconds, the gel will be loosened from the glass plate and fall ideally onto the filter paper.

4) Turn off the water and remove the glass plate and wash it up.

4a, an optional step) Continue the water flow until the water level in the tray is at or just over the level of the gel. Do not keep the water on any longer, or it will force the gel to curl under. Leave 5 minutes to allow urea and other heavy solutes (such as sucrose), that interfere with subsequent drying, to literally fall out of the gel into the water wash, and then open the tray drain and lower the water level to ½ the height of the support grid.

5) The gel may be fixed in a separate step as follows: Lift up the gel on the filter paper and place it onto another sheet of filter paper that has just been wet with 15 to 20% acetic acid. Wait 5 minutes, perhaps with indicator drops as described below.

5a) Alternatively, the gel may be fixed as follows: Add 20% acetic acid to the tray (or other appropriate amount and concentration) to raise the level of the fluid to the top of the support grid, which is the bottom of the gel. Lift the gel by grasping the outer carrier frame and tilt the tray to mix in the acid. Allow the gel to sit in contact with the acetic acid for at least 5 minutes. Additional (beneficial) loss of urea will occur during this period.

Indicator Drops

To ensure that the time of fixing has been adequate, put a drop of 0.1% bromophenol blue in 50 mM Tris 2" from the each corner on the top surface of the gel, to serve as indicator. This indicator will turn green when the acetic acid has permeated the gel, usually in only about 5 minutes.

6) Apply the Saran wrap and dry under vacuum as usual.

All publications mentioned in this specification are indicative of the level of skill of those skilled in the art to which this invention pertains. These publications are herein incorporated by reference to the same extent as if each individual publication were specifically and individually indicated to be incorporated by reference.

The invention now being fully described, it will be apparent to one of ordinary skill in the art that many changes and modifications can be made thereto without departing from the spirit or scope of the appended claims.

LITERATURE CITED

Ausubel, F. M., Brent, R., Kingston, R. E., Moore, D. D., Seidman, J. G., Smith, J. A. and Struhl, K. (1989) *Current Protocols in Molecular Biology*, John Wiley and Sons, N.Y. Sambrook, J., Britsch, E. F., and Maniatis, T. (1989) chapter 13.56 of 2d edition of *Molecular Cloning—a laboratory manual*, Cold Spring Harbor Laboratory Press.

What is claimed is:

1. Apparatus for aiding removal of a gel from the surface of a plate, comprising:
    a generally horizontal frame having an upper surface defining an inner open area, said frame comprising a liquid inlet, a channel, and a plurality of liquid outlets, said inlet, channel and outlets all being in liquid communication to allow a liquid entering said inlet to pass through said channel to said outlets; wherein each said outlet is constructed and arranged to cause liquid passing through said outlets to be projected toward said inner open area; and wherein said frame is adapted to hold a plate generally horizontally over said inner open area; and
    a generally horizontal grid positioned below said inner open area, and adapted to hold a sheet of filter paper in a generally horizontal position below said inner open area; wherein said grid and frame are positioned relative to each other to allow a gel on the under surface of said plate to be removed by liquid flowing from said outlets, and fall onto the upper surface of said grid.

2. The apparatus of claim 1 wherein said outlets are constructed and arranged to project liquid passing through said outlets above said upper surface of said frame.

3. The apparatus of claim 1 wherein said frame further comprises a bracket adapted to hold the plate above said upper surface of said frame.

4. The apparatus of claim 1 further comprising a second generally horizontal frame adapted to hold said grid and said frame generally horizontally and spaced from each other.

5. A method for removing a gel from the surface of a plate, comprising the steps of:
    providing an apparatus comprising a generally horizontal frame having an upper surface defining an inner open area,
    said frame comprising a liquid inlet, a channel, and a plurality of liquid outlets, said inlet, channel, and outlets all being in liquid connection to allow a liquid entering said inlet to pass through said channel to said outlet; wherein each said outlet is constructed and arranged to cause liquid passing through said outlets to be projected towards said inner open area; and wherein said frame is adapted to hold the plate generally horizontally over said inner open area; and a generally horizontal grid positioned below said inner open area, and adapted to hold a sheet of filter paper in a generally horizontal position below said inner open area; wherein said grid and frame are positioned relative to each other to allow a gel on the undersurface of said plate to be removed by liquid flowing from said outlets, and fall onto the upper surface of said grid;
    placing the plate above the frame and over said inner open area with the gel located on the surface of the plate closest to the liquid outlets; and
    causing a liquid to be projected from said liquid outlets towards the gel to thereby cause the gel to be removed from the plate and fall toward said grid.

6. The method of claim 5 wherein said method further comprises placing a sheet of filter paper on the upper surface of said grid in a position suitable for contacting said gel when it is removed from the plate.

7. The method of claim 6 wherein said liquid is caused to flow from said outlets onto said filter paper prior to placing the plate in a position above said inner open area.

8. The method of claim 5 wherein said liquid is caused to flow from said outlets after removal of the gel from the plate to provide sufficient liquid to aid in removal of diffusable substances in said gel.

* * * * *